(12) United States Patent
Exner et al.

(10) Patent No.: US 11,488,038 B2
(45) Date of Patent: Nov. 1, 2022

(54) METHOD AND DEVICE FOR MONITORING

(71) Applicant: SONY CORPORATION, Tokyo (JP)

(72) Inventors: Peter Exner, Malmö (SE); Anders Isberg, Lund (SE)

(73) Assignee: SONY NETWORK COMMUNICATIONS EUROPE B.V., Hoofddorp (NL)

( * ) Notice: Subject to any disclaimer, the term of this patent is extended or adjusted under 35 U.S.C. 154(b) by 482 days.

(21) Appl. No.: 16/825,828

(22) Filed: Mar. 20, 2020

(65) Prior Publication Data

US 2020/0311577 A1   Oct. 1, 2020

(30) Foreign Application Priority Data

Mar. 29, 2019 (SE) .................................. 1950398-6

(51) Int. Cl.
| | |
|---|---|
| G06Q 10/04 | (2012.01) |
| A61B 5/00 | (2006.01) |
| G05B 13/04 | (2006.01) |
| G06N 5/04 | (2006.01) |
| G16H 40/67 | (2018.01) |

(Continued)

(52) U.S. Cl.
CPC ........... G06N 5/04 (2013.01); A61B 5/14532 (2013.01); A61B 5/7264 (2013.01); A61B 5/7275 (2013.01); G01R 21/133 (2013.01); G06N 20/00 (2019.01); G06Q 10/04 (2013.01);

(Continued)

(58) Field of Classification Search
None
See application file for complete search history.

(56) References Cited

U.S. PATENT DOCUMENTS

2008/0169968 A1*   7/2008   Easthope .............. G01S 13/726
                                                                    342/95
2009/0069642 A1    3/2009   Gao et al.
(Continued)

FOREIGN PATENT DOCUMENTS

CN        109171756 A      1/2019
WO          0215777 A1     2/2002
(Continued)

OTHER PUBLICATIONS

European Search Report from corresponding European Patent Application No. 20157745, dated Aug. 11, 2020, 2 pages.
(Continued)

*Primary Examiner* — Curtis A Kuntz
*Assistant Examiner* — Jerold B Murphy
(74) *Attorney, Agent, or Firm* — Tucker Ellis LLP

(57) ABSTRACT

A method for monitoring a primary variable is carried out in a device having access to a set of sensors. The method includes the steps of receiving, from a network service, a series of forecasted values for the primary variable, each forecasted value being associated with one of a series of future time points; for at least one of the future time points, predicting a value for the primary variable using data of at least one secondary variable captured by a subset of the set of sensors, comparing the predicted value to the forecasted value associated with the future time point, and switching to a different subset of the set of sensors, if the predicted value deviates from the forecasted value with more than a specified threshold value.

20 Claims, 3 Drawing Sheets

(51) Int. Cl.
*G06N 20/00* (2019.01)
*A61B 5/145* (2006.01)
*G01R 21/133* (2006.01)
*G06Q 50/06* (2012.01)
*H04Q 1/02* (2006.01)

(52) U.S. Cl.
CPC ............ *G06Q 50/06* (2013.01); *G16H 40/67* (2018.01); *H04Q 1/03* (2013.01)

(56) References Cited

U.S. PATENT DOCUMENTS

| | | |
|---|---|---|
| 2009/0177068 A1 | 7/2009 | Stivoric et al. |
| 2014/0171749 A1 | 6/2014 | Chin et al. |
| 2018/0158019 A1 | 6/2018 | Vutukuri et al. |
| 2019/0050948 A1 | 2/2019 | Perry et al. |

FOREIGN PATENT DOCUMENTS

| | | |
|---|---|---|
| WO | 2013085459 A1 | 6/2013 |
| WO | 2018086133 A1 | 5/2018 |
| WO | 2018169374 A1 | 9/2018 |

OTHER PUBLICATIONS

Swedish Office Action and Search Report from corresponding Swedish Application No. 1950398-6, dated Oct. 9, 2019, 8 pages.

* cited by examiner

METHOD AND DEVICE FOR MONITORING

RELATED APPLICATION DATA

This application claims the benefit of Swedish Patent Application No. 1950398-6, filed Mar. 29, 2019, the disclosure of which is incorporated herein by reference in its entirety.

TECHNICAL FIELD

The present disclosure generally relates to the field of monitoring, and more specifically to a method and a device for monitoring a primary variable.

BACKGROUND ART

Intelligent monitoring systems are used in all fields of technology. They generally include sensors for measuring different variables and computers for processing data from the sensors. Some sensors are battery-powered. Depending on the location of the sensor or the type of sensor, it can sometimes be difficult to replace the battery or to recharge it. Therefore power conservation is an important aspect in many monitoring systems.

In some monitoring systems, data is exchanged over the Internet between monitoring devices and network servers. For a battery-powered monitoring device, the radio transceiver may be one of the most power-consuming elements. In some systems it may therefore be desirable to limit the use thereof.

US 2018/0158019 relates to an asset tracking device which includes a processor configured to compare a current transport status to a predicted transport status at each respective time instance of a plurality of time instances. In response to determining that the current transport status does not differ from the predicted transport status by greater than a specified threshold, the processor skips sending a report relating to the current transport status to a service over a network. In this way battery power of the asset tracking device is conserved. The predicted transport status can be computed by the asset tracking device, or alternatively by a remote service and transmitted to the asset tracking device by the service.

SUMMARY

It is an objective to at least partly overcome one or more limitations of the prior art.

Another objective is to provide a monitoring device which operates in a battery-saving way.

Yet another objective is to enable battery power conservation in sensors used in a monitoring system.

One or more of these objectives, as well as further objectives that may appear from the description below, are at least partly achieved by a method and a device according to the independent claims, embodiments thereof being defined by the dependent claims.

According to one aspect, a method is provided for monitoring a primary variable, the method being carried out in a device having access to a set of sensors, comprising receiving, from a network service, a series of forecasted values for the primary variable, each forecasted value being associated with one of a series of future time points; and, for at least one of the future time points, predicting a value for the primary variable using data of at least one secondary variable captured by a subset of the set of sensors, comparing the predicted value to the forecasted value associated with the future time point, and switching to a different subset of the set of sensors, if the predicted value deviates from the forecasted value by more than a specified threshold value.

According to another aspect a device is provided for monitoring a primary variable, comprising a processor and a communication interface, the device having access to a set of sensors, wherein the communication interface is configured to receive, from a network service, a series of forecasted values for the primary variable, each forecasted value being associated with one of a series of future time points, wherein the processor is configured to, for at least one of the future time points, predict a value for the primary variable using data of at least one secondary variable captured by a subset of the set of sensors, compare the predicted value to the forecasted value associated with the future time point, and switch to a different subset of the set of sensors, if the predicted value deviates from the forecasted value by more than a specified threshold value.

To sum up, a first sensor subset is used as long as the value predicted by the data from the first sensor subset is sufficiently close to the corresponding forecasted value.

When the deviation becomes too large, processing is continued with another sensor subset. In this way the use of the sensors can be optimized so that less power consuming sensors and/or sensors in which the battery is easier to replace or recharge are used as long as the prediction is good enough, and so that more power consuming sensors and/or sensors for which battery power conservation is more important are used only when positively required.

Still other objectives, features, aspects and advantages will appear from the following detailed description, from the attached claims as well as from the drawings.

BRIEF DESCRIPTION OF DRAWINGS

Embodiments of a method and a device for monitoring will now be described in more detail with reference to the accompanying schematic drawings.

DETAILED DESCRIPTION OF EXAMPLE EMBODIMENTS

In the following, a device and a method for monitoring a primary variable are disclosed by way of examples.

Figure 1:
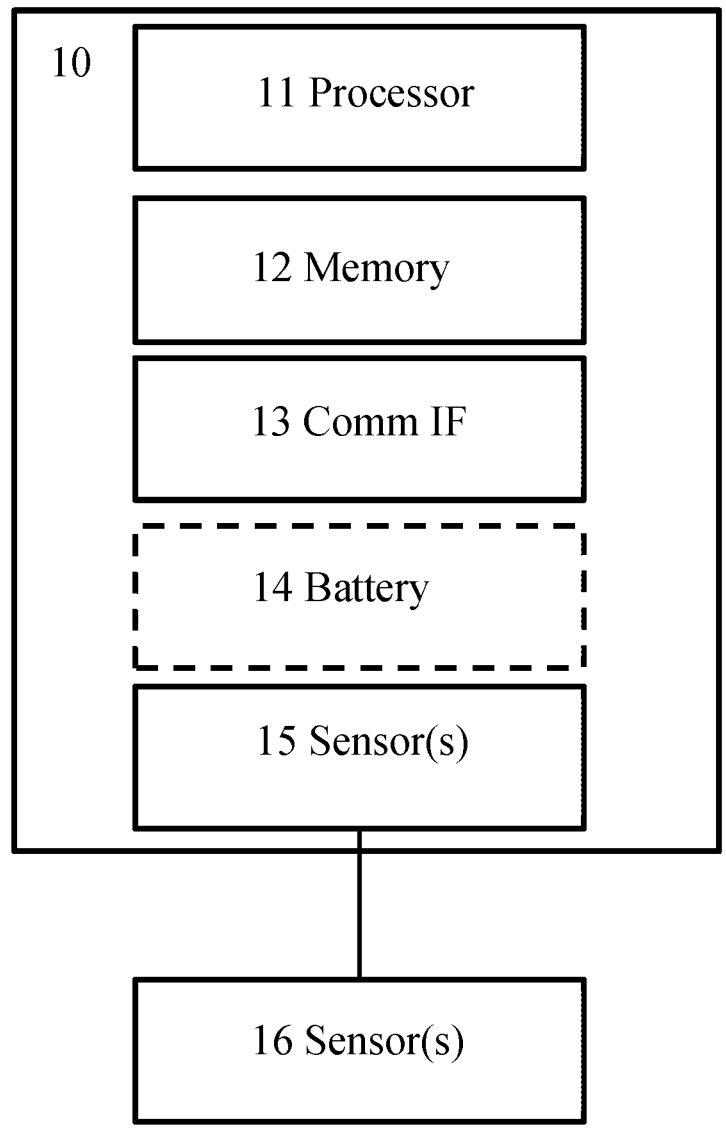
FIG. 1 is a block diagram of one embodiment of a device for monitoring a primary variable.

FIG. 1 schematically shows an embodiment of a monitoring device 10 comprising a processor 11, a memory 12, a communication interface 13, a battery 14 and one or more internal sensors 15 and/or one or more external sensors 16. These parts of the monitoring device 10 are functionally and operatively connected to each other as is well understood by the skilled person.

The processor 11 may be a generic processor, e.g. a microprocessor, microcontroller, CPU, DSP (digital signal processor), GPU (graphics processing unit), etc., or a specialized processor, such as an ASIC (application specific integrated circuit) or an FPGA (field programmable gate array), or any combination thereof.

The memory 12 may include volatile and/or non-volatile memory such as read only memory (ROM), random access memory (RAM) or flash memory. It may store instructions which, when executed by the processor 11, causes the processor to perform the steps of the monitoring method described herein. It may also store any data used for performing the method and any data resulting from the performing of the method.

The communication interface 13 may comprise software and/or hardware to control sending and receiving of data to and from one or more external units. It may be configured for data exchange over a Wide Area Network, such as the Internet. For that purpose, it may comprise a wireless transceiver or transmitter-receiver. Via the communication interface 13, the monitoring device 10 may for instance exchange data with a network service, as will be further explained below.

In some embodiments, the communication interface 13 may additionally be configured for wireless short-distance communication with external components, such as the external sensor(s) 16. Communication may e.g. occur via Bluetooth, IrDA (Infrared Wireless), UWB (Ultra Wideband), Induction wireless technology, or similar technology.

In still other embodiments, the communication interface 13 may also allow for direct data transfer through a cable.

The battery 14 powers the monitoring device 10. It may also drive the sensors 15, 16. Alternatively, one or more of the sensors may have their own batteries. Depending on where the monitoring device 10 is located and how it is designed, it may be more or less difficult to replace the battery when it is discharged. The same goes for any battery of the sensors. In other embodiments, the monitoring device 10 may be powered from an external power source.

The monitoring device 10 has access to a set of sensors comprising at least two sensors 15, 16. In some embodiments, one or more of the sensors are internal 15, i.e. integrated in the device. In other embodiments, one or more of the sensors are external 16, i.e. located outside the device, but accessible by the device, by wire or wirelessly, so that measurement values/data from the sensors 16 can be captured by the monitoring device 10. In yet other embodiments, there are at least one internal sensor 15 and at least one external sensor 16.

The sensors 15, 16 form a set of sensors. From the set of sensors, different subsets may be defined. Each subset may include one sensor, some of the sensors but not all sensors, or all sensors. In some embodiments, there is no common sensor between the different subsets, i.e. each sensor is included in only one subset. In other embodiments, a sensor may be included in more than one subset, and may even be included in all sub sets.

In some embodiments, each sensor 15, 16 of the set of sensors is configured to sense a respective secondary variable, which is correlated to the primary variable and which thus can be used to calculate or predict the primary variable. In other embodiments, two or more sensors may sense one and the same secondary variable. In such cases, the sensors may be differently designed and configured to sense the secondary variable with different confidence levels and/or with different power consumption levels. The set of sensors 15, 16 may, but need not, also include at least one sensor for measuring the primary variable.

The sensors 15, 16 are used in different combinations and in different selected sequences to achieve a power efficient monitoring. More specifically, a predetermined number of subsets of the set of sensors may be ordered in a predetermined order or sequence. The predetermined number, which is at least two, may or may not include all possible subsets of the set of sensors. Generally, the subsets will be ordered so that each next subset in the sequence will result in a predicted value for the primary variable having a higher confidence level than what was achieved with the previous subset. A higher confidence level may, for instance, be achieved by successively adding sensors to the subsets. Alternatively it may be achieved by switching from one or more sensors measuring one or more first secondary variables to one or more different sensors measuring the same or one or more other secondary variables with a better correlation to the primary variable. As a secondary criterion, the subsets included in the predetermined order may be selected and ordered based on power consumption and/or power conservation. Generally, it may be desirable to have a subset of sensor(s) with a relatively high power consumption towards the end of the predetermined order so that such a subset is only used when needed. The same goes for a subset with one or more sensors for which battery power conservation is essential.

The predetermined order of subsets of the set of sensors may be prestored in the memory 13 of the device 10, i.e. at manufacture, or downloaded to the monitoring device 10 when the device is initialized. The predetermined order may be fixed or dynamic. In the latter case it can be changed by the processor 11 of the monitoring device or updated from a network service.

In an embodiment, a monitoring device 10 has access to a set of four sensors 15, 16. The sensors are denoted A, B, C and D. In one predetermined sequence, the sensors are successively added, so that the sequence is A; AB, ABC; ABCD. In another sequence, they are used one by one in succession, so that the sequence is A; B; C; D. In yet another sequence, only some of the sensors are used and they are used in different combinations so that the sequence is A; AB; D. These examples are in no way exhaustive. They are only given to illustrate different ways of ordering subsets of a set of sensors.

The monitoring device 10 receives a plurality of forecasted values for the primary variable via its communication interface 13. The forecasted values are sent by a network service. They may be received directly from the network service or through the intermediary of another unit to which they have been transferred from the network service.

As used herein, the network service is meant to include any service implemented in a network environment. It specifically includes all kinds of cloud services. The network service may be implemented on a network unit such as a dedicated network server or a cloud server. The network unit may comprise at least one processor, memory and a communication interface for sending and receiving data to and from the monitoring device 10 via a network, such as the Internet. The processor may run a network service software to handle the processes described herein.

In some embodiments, the monitoring device 10 may be part of a larger network of devices, which in turn may be part of the Internet of Things (IoT), which allows traditionally non-internet-enabled physical devices to be connected to the Internet. The monitoring device 10 can thus in such cases be defined as an IoT device. Furthermore, the network unit may be an Internet of Things server or an Internet of Things Edge or Internet of Things Node.

The network service may include a forecasting model for forecasting the series of future values of the primary variable. The forecasting model may be trained using machine learning and/or Artificial Intelligence. The training may be based on historical data from a large number of devices similar to the monitoring device 10. Data from other sources, such as demographic data, geographic data, and climate data, may also be used for the training. The forecasting model may be continuously refined as new training data becomes available.

The monitoring device 10 may use a prediction model for predicting values of the primary variable based on data of at least one secondary variable captured from a subset of the set of sensors. The prediction model may be installed at the time of manufacturing. It may also be received from the network service, e.g. when the monitoring device 10 is initialized. The prediction model may be a simpler version of the forecasting model used by the network service, taking the more limited capabilities of the monitoring device into account. It may be trained by the network service based on similar data. The prediction model may be static once installed in the device or it may be updated from the network service during operation. In addition to current sensor data, it may also take historical sensor data and historical predicted values as input.

The forecasting model and the prediction model may be deterministic or non-deterministic (i.e. probabilistic). They may use different models/algorithms for the forecasting/prediction such as at least one of a linear regression model, a recurrent neural network, a Bayesian classification model, a support-vector machine and a random forest algorithm.

As used in this application, the expressions "forecasting" and "prediction" have the same meaning, i.e. calculation or estimation of future values of a parameter or variable. However, for readability reasons, "forecasting" is used for calculation of future values by the network service 22, whereas "prediction" is used for calculation of future values by the monitoring device 10.

The monitoring device 10 may include a clock function to keep track of the current time. The clock function may be implemented in a hardware and/or a software component.

Figure 2:
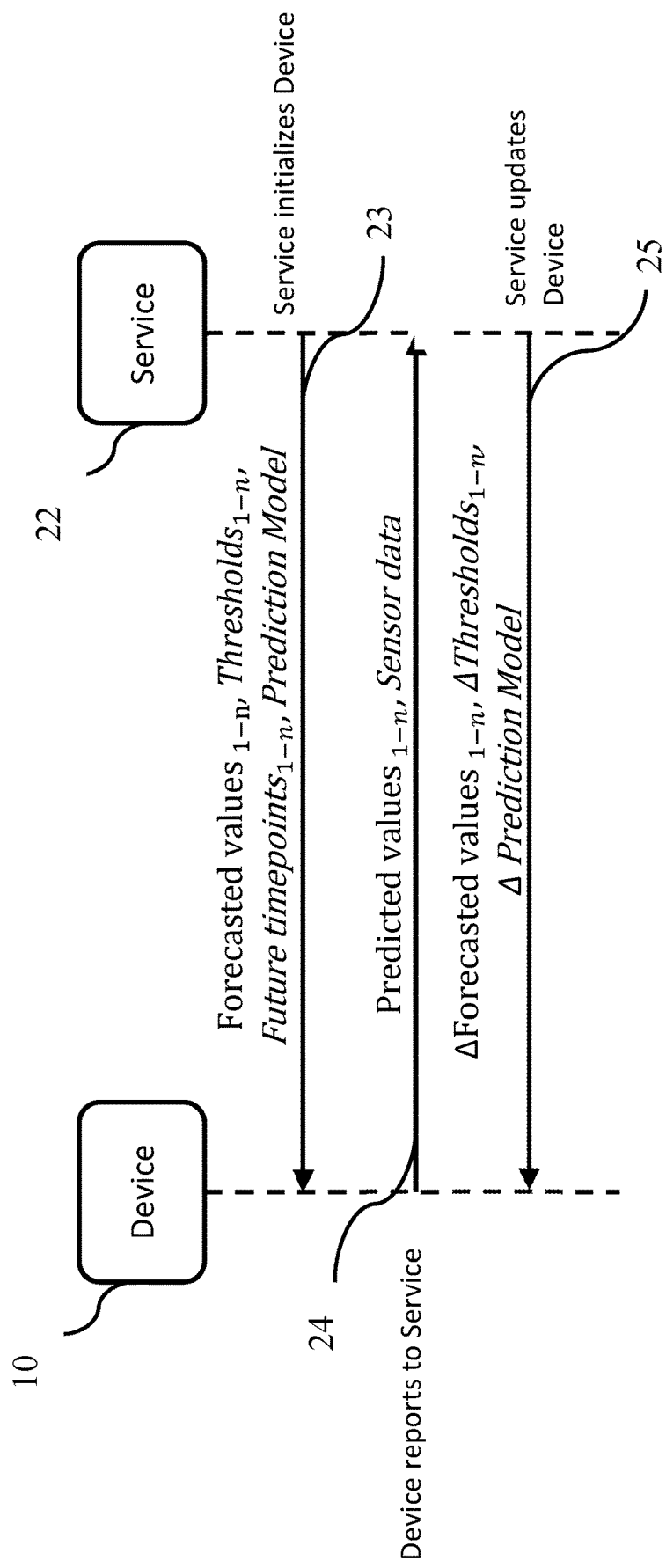
FIG. 2 is a sequence diagram showing an example of data exchange between a monitoring device and a cloud service.

FIG. 2 is a sequence diagram which schematically shows a data exchange between a monitoring device 10 (in the following also referred to simply as a "device") for monitoring a primary variable and a network service 22 (in the following also referred to simply as a "service").

In this example, there are three main steps 23-25, symbolized by arrows, in the data exchange between the monitoring device 10 and the network service 22: In a first step 23, the service initializes the device, in a second step 24, the device reports to the service, and in a third step 25, the service updates the device.

In the initialization step 23, the service 22 sends a series of n forecasted values (1 to n) for the primary variable to the monitoring device 10. The series of forecasted values has been forecasted by the service 22, using a forecasting model as described above. The number of forecasted values n in the series is at least two.

Each forecasted value is associated with one future time point in a series of n future time points (1 to n). The series of future time points may be sent to the monitoring device 10 together with the series of forecasted values. In some embodiments, the future time points are predetermined and are previously stored in the device. In some embodiments, they are represented with a starting time point and a fixed interval between subsequent time points. In some embodiments, the intervals between the future time points may vary.

The initialization step 23, may also comprise sending a prediction model to the device. As already mentioned, the prediction model may be a less complex version of the forecasting model.

The initialization data may also include one or more threshold values to be used by the device as will be further explained below. In the embodiment of FIG. 2, a series of n threshold values (1 to n) are sent to the device, where each threshold value is associated with a forecasted value.

In some embodiments and depending on the type of primary variable to be monitored, there may be a pre-initialization step (not shown in FIG. 2) where the device 10 sends data to the service 22, which uses the received data as input to the forecasting model. The data may comprise historic and/or current sensor data, including values of secondary variables and/or the primary variable, as well as predicted values and any other relevant data available to the device. The purpose of the pre-initialization step is to enable more accurate initial forecasting of values for the primary variable.

When the monitoring device 10 has been initialized, the device operates independently of the service 22 and without sending any data to the service until a reporting criterion is met. Since the network communication interface 13 can be held in low power mode or be deactivated, battery power of the monitoring device may be saved.

The operation of the device comprises, for at least one of the future time points, predicting a value for the primary variable using data of at least one secondary variable captured by a subset of the set of sensors, comparing the predicted value to the forecasted value associated with the future time point, and switching to a different subset of the set of sensors, if the predicted value deviates from the forecasted value with more than a specified threshold value.

The specified threshold value may be a threshold value that was previously stored in the memory 12 of the device 10, e.g. at manufacturing. In some embodiments, the specified threshold value is received from the service 22, e.g. when the device is initialized. The specified threshold value may be a fixed value or it may be updated during the operation by the service 22.

In some embodiments, the specified threshold value is a threshold value in a series of threshold values received from the service. Each threshold value in the series may be associated with a respective forecasted value. At least two of the threshold values in the series may be different.

In one embodiment, the specified threshold value is one of a plurality of threshold values, where each threshold value is associated with a respective sensor subset. In this way account may be taken to the different confidence levels of the sensor subsets.

One reporting criterion may be that a predetermined number of subsets of the set of sensors has been used. As mentioned above, different subsets of the set of sensors may be ordered in a predetermined order depending on one or more characteristics, such as confidence level, power consumption and power conservation. When all subsets in the predetermined order has been used and a threshold value is exceeded, there may be no way of providing a prediction of the value of the primary variable with higher confidence, and therefore the device 10 needs to report to the network service 22 to get a series of updated forecasted values.

Another reporting criterion may be that all the future time points, or a predetermined number thereof, have been reached, so that there is no or few further forecasted values of the primary variable left. The device may then report to the service to receive a set of updated forecasted values. In other embodiments, the service may keep track of the future time points and send updated forecasted values to the device without receiving any report from the device.

Yet another reporting criterion may be that the difference between the predicted value and the forecasted value exceeds a predetermined reporting threshold value that is larger than the threshold value used for determining if the current sensor subset should be switched to the next sensor subset in the predetermined order. This threshold value could be used as a safety measure to detect abnormal conditions that should be reported to the network service 22. The predetermined reporting threshold value may be pre-stored in the memory 12 of the device 10 or may be received from the network service 22 as initialization data.

When the reporting criterion is met, the device 10 reports to the service 22 in reporting step 24. The report includes at least some of the values for the primary variable that have been predicted since the last report. In some embodiments, the report also includes historic and/or current sensor data. The sensor data may include values of secondary variables used as input to the prediction model of the device, and/or any measured value of the primary variable.

When the service receives the reported data from the device, it uses the reported data as input to the forecasting model. An updated series of forecasted values for the primary variable is calculated. In the updating step 25, the newly forecasted values are sent to the device, optionally together with any of one or more new threshold values, new future time points, an updated predetermined order of the subsets, and any other relevant data. Also, the prediction model used in the device may be updated by the network service 22 and sent to the device 10 in the updating step 25.

The reporting step 24 and the updating step 25 may be repeated during the continued operation of the device.

The data exchange between the monitoring device 10 and the service 22 may include other steps. The service may for instance detect an abnormal condition that may affect the operation of the device. Such a condition may be detected using data from other data sources than the device. When such a condition is detected, the service may contact the device and request a report. This report may be a predetermined special report or the report that is sent when the reporting criterion is met. In another embodiment the service sends updated data to the device when an abnormal condition is detected.

Figure 3:
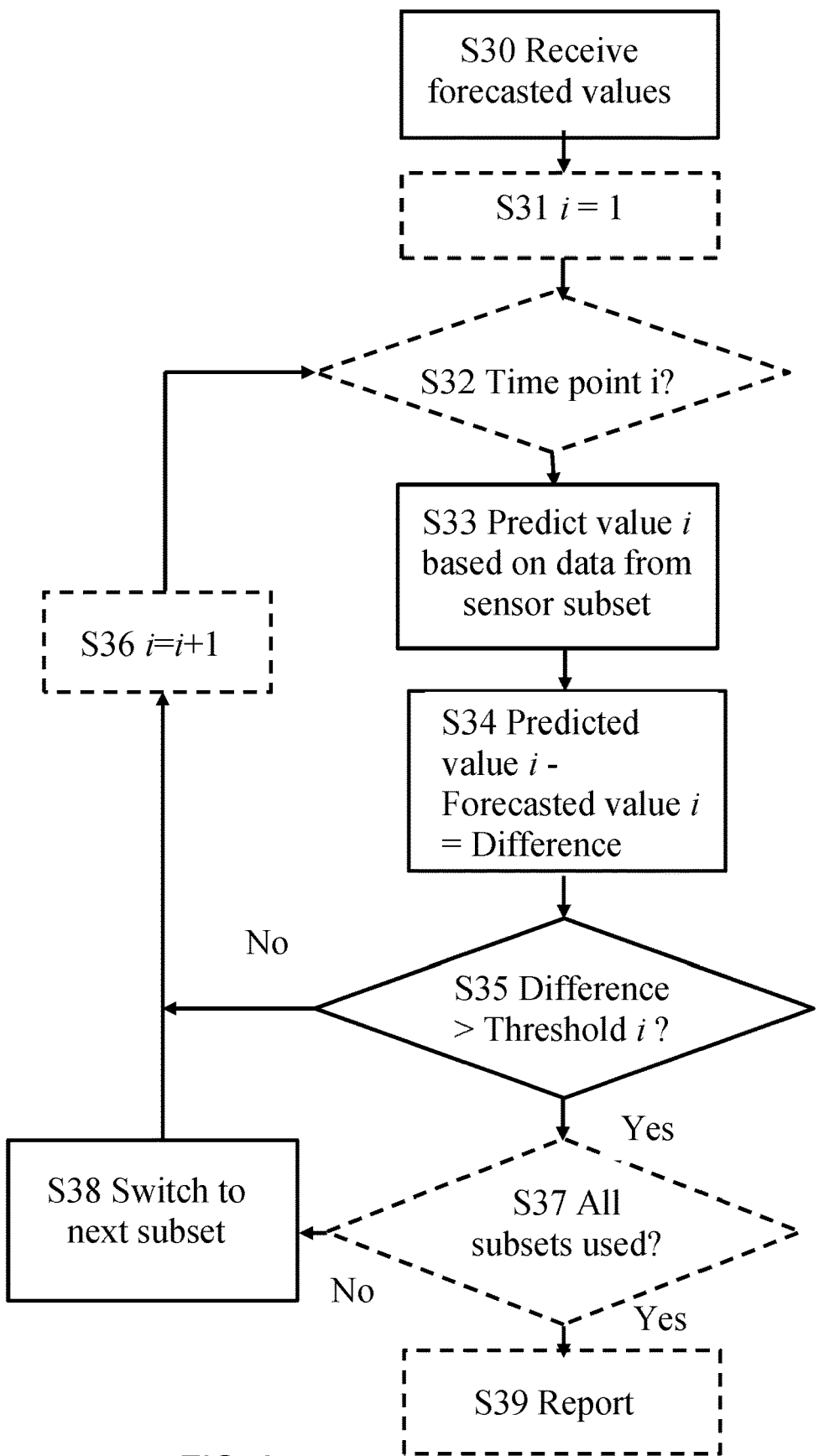
FIG. 3 is a flow chart of one embodiment of a method for monitoring a primary variable.

FIG. 3 is a flow chart showing one embodiment of a method for monitoring a primary variable, the method being carried out in a monitoring device, like the monitoring device 10 in FIG. 1.

In a first step S30, the monitoring device receives a series of forecasted values (1 to n) for a primary variable from a network service 22. Each forecasted value i is associated with a future time point i in a series of future time points.

In step S31, the future time point i is set to 1.

In step S32, the clock function of the monitoring device 10 checks whether the current time has reached future time point 1. If not, the check is carried out anew until future time point 1 has been reached. Then the flow continues to step S33.

In step 33, the device captures data from a first subset of the set of sensors. The first subset is selected according to the predetermined order of subsets store in the device. The data captured from the first subset of sensors refers to one or more secondary variables that correlate with the primary variable to be monitored. The captured data is input to the prediction model stored in the device. The prediction model outputs a predicted value for the primary variable for future time point i=1. In step S34, the predicted value for time point i=1 is compared to the forecasted value for time point i=1. The comparison results in a difference or deviation, which is zero if the predicted value and the forecasted value are equal.

In step S35, the difference is compared to the threshold associated with the time point i=1. If the difference does not exceed the threshold value, the prediction is considered to be adequate and the monitoring device continues to operate in the same manner independently of the service 22. More particularly, the future time point i is updated to i=i+1 in step S36. Then the process awaits that the current time reaches the updated time point i=i+1, i.e. the second time point, and then steps S33-S35 are repeated. This loop consisting of steps S32-S36 is continued as long as the difference between the predicted value and the forecasted value is less than the corresponding threshold value.

If, however, in step S35, the difference exceeds the threshold associated with the current time point i, the prediction is considered to have an insufficient confidence level, and the process continues to step S37, in which it is checked whether all subsets in the predetermined sequence have been used. If this is not the case, the device, in step S38, switches to the next subset in the predetermined sequence, e.g. by disabling the sensors in the current subset that are not part of the subsequent subset and by enabling the sensors in the subsequent subset that are not part of the current subset. The future time point i is updated in step S36 and the loop consisting of steps S32-S36 is continued with the new current subset of sensor(s) as long as the difference between the predicted value and the forecasted value does not exceed the corresponding threshold value.

Steps S32-S38 are repeated until it is established in step S37 that all the subsets in the predetermined sequence have been used. Then, in step S39, the device 10 sends a report to the network service 22.

When network service 22 transmits a new series of forecasted values for the primary variable, the process starts all over again by step S30.

The device and the methods described above are generally applicable for monitoring in many different technical fields. Below some examples will be given.

The device and the method for monitoring may be used in the medical field to monitor different conditions in the human body. Sensors applied in or on the human body may have batteries that are difficult to replace or recharge, and in such cases battery power conservation is essential. One example is monitoring of blood glucose values by a sensor that is placed under the skin of a diabetic to measure blood glucose levels in the interstitial fluid. The blood glucose sensor may communicate via Bluetooth with a monitoring device designed as a wearable device, which in turn may communicate with a network service that provides forecasted values of the blood glucose level of the diabetic. In one embodiment, the monitoring device has access to a set of sensors for measuring body temperature, heart rate, blood pressure and skin impedance. These variables are secondary variables correlated to the primary variable, i.e. the blood glucose level, so that blood glucose values can be predicted therefrom. The set of sensors also include the actual sensor for measuring blood glucose levels.

The sensors are used in subsets. The subsets may be ordered in a predetermined sequence, which in some embodiments is as follow: Subset 1: sensors for measuring body temperature and heart rate, Subset 2: sensors for measuring body temperature, heart rate, blood pressure and skin impedance. Subset 3: sensors for measuring body temperature, heart rate, blood pressure, skin impedance and blood glucose level. In this example, subset 2 includes all the sensors of subset 1, and subset 3 includes all the sensors of subset 2. Also subset 3 includes all sensors of the set of sensor to which the device has access, i.e. all available sensors. In this example, subset 1 has low power consumption, subset 2 has an intermediate power consumption, and subset 3 has a high power consumption.

In the example above, the sensor for measuring the primary variable, i.e. the blood glucose level, could be disabled or held in low power mode, as long as the data from the sensors of the secondary variables results in a predicted value of the blood glucose level that does not deviate from the corresponding forecasted value of the blood glucose level with more than a specified threshold value. Only when the two first sensor subsets have been used and the deviation exceeds the specified threshold value, is the blood glucose sensor activated. In this way, battery power of the blood glucose sensor can be conserved. Also, battery power of the wearable monitoring device can be saved since the monitoring device can operate independently of the network service as long as the predicted values stay within specified normal conditions as reflected by the threshold values. Moreover, using sensor subsets ordered according to power consumption, may save battery power for sensors powered from the monitoring device.

Another example where the device and the method for monitoring can be used is within the field of agriculture to monitor growth of different plants and crops. In one monitoring system, the growth is monitored by a camera, connected to or included in a monitoring device, which communicates with a network service. In order to save the battery of the camera, the monitoring device has access to one or more sensors that are less power consuming, the one or more sensors are for measuring secondary variables, such as soil moisture, air humidity, soil temperature, air temperature, and UV radiation. At least two subsets of the set of sensors are ordered in a predetermined order with the camera included in the last subset in the order. As long as the growth predicted from subset(s) of the sensor(s) sensing the secondary variable(s) does not deviate from the forecasted growth values received from the network service with more than a specified threshold value, the camera need not be used. Not until the deviation exceeds the threshold value and all subsets except the last one with the camera have been used, is the camera enabled. If the difference between the growth predicted by the last subset including the camera on the one hand and the forecasted growth value on the other hand exceeds the threshold value, the monitoring device sends a report to the network service including predicted growth values and values measured by the sensors.

Yet another example comes from the field of transportation and logistics. A cargo transport vehicle monitoring system monitors the position of a vehicle during its predetermined route to a destination. The system comprises a monitoring device located in the vehicle and having access to a set of sensors, as well as a network service. The sensor for measuring the primary variable, which in this case is the position of the vehicle, is a GPS (Global Positioning System). In order to conserve power of the battery of the GPS, the monitoring device has access to at least one other sensor that senses a secondary variable from which the position of the vehicle can be predicted. The secondary variable may e.g. be one of fuel consumption, acceleration, and distance travelled.

Subsets of the sensors are ordered in a predetermined order with the GPS included in the last subset in the order. As long as the vehicle position predicted from data from one or more of the subset(s) of the sensor(s) sensing the secondary variable does not deviate from the corresponding forecasted position received from the network service with more than a specified threshold value, the GPS need not be used. Not until the deviation exceeds the threshold value and all other sensor subsets that do not include the GPS have been used, the GPS is enabled. If the difference between the vehicle position predicted by the last subset including the GPS on the one hand and the forecasted vehicle position on the other hand exceeds the threshold value, the monitoring device sends a report to the network service including predicted positions and current and historical values measured by the sensors.

Items

Item 1: A method for monitoring a primary variable, the method being carried out in a device having access to a set of sensors (15, 16), comprising
    receiving (S30), from a network service (22), a series of forecasted values for the primary variable, each forecasted value being associated with one of a series of future time points;
characterized by
    for at least one of the future time points, predicting (S33) a value for the primary variable using data of at least one secondary variable captured by a subset of the set of sensors, comparing (S34) the predicted value to the forecasted value associated with the future time point, and switching (S38) to a different subset of the set of sensors, if the predicted value deviates from the forecasted value with more than a specified threshold value.

Item 2: A method according to item 1, wherein the predicting (S33) and the comparing (S34) are repeated for a subsequent future time point using the same subset of the set of sensors (15, 16), if the predicted value deviates from the forecasted value with less than the specified threshold value.

Item 3: A method according to item 1 or 2, wherein a predetermined number of subsets of the set of sensors are ordered in a predetermined order and wherein switching (S38) to a different subset of the set of sensors comprises switching (S38) to the next subset according to the predetermined order.

Item 4: A method according to item 3, wherein the predetermined order is based on prediction confidence.

Item 5: A method according to item 3 or 4, wherein the predetermined order is based on power conservation.

Item 6: A method according to item 3 or 4, wherein the predetermined order is based on power consumption.

Item 7: A method according to any one of items 3-6, wherein the predetermined order is received from the network service (22).

Item 8: A method according to any one of items 3-7, wherein at least one sensor in the set of sensors is included in more than one subset in the predetermined order of sub sets.

Item 9: A method according to any one of the preceding items, comprising reporting (S39) to the network service, if a specified number of subsets of the set of sensors (15, 16) has been used.

Item 10: A method according to any one of the preceding items, comprising reporting (24) to the network service (22) if the difference between the predicted value and the forecasted value exceeds a predetermined reporting threshold value.

Item 11: A method according to item 9 or 10, comprising receiving (25), in response to the reporting, an updated series of forecasted values for the primary variable.

Item 12: A method according to item 9, 10 or 11, wherein at least one subset of sensors (15, 16) comprises a sensor for measuring the primary variable, and reporting (24; S38;) comprises reporting a current value of the primary variable to the network service (22).

Item 13: A method according to any one of the preceding items, wherein receiving comprises receiving (23) a series of threshold values.

Item 14: A method according to item 13, wherein each threshold value of the series of threshold values is associated with a future time point.

Item 15: A method according to item 13 or 14, wherein at least two threshold values in the series of threshold values are different.

Item 16: A method according to any one of the preceding items, comprising receiving (23), from the network service, a prediction model, and using the prediction model for predicting the value of the primary variable using data of at least one secondary variable captured by a subset of the set of sensors (15, 16).

Item 17: A method according to item 16, wherein the prediction model is based on at least one of a linear regression model, a recurrent neural network, a classification model, a support-vector machine and a random forest algorithm.

Item 18: A method according to any one of the preceding items, wherein the primary variable is a blood glucose level.

Item 19: A device for monitoring a primary variable, comprising a processor (11) and a communication interface (13), the device having access to a set of sensors (15, 16), wherein the communication interface (13) is configured to receive, from a network service (22), a series of forecasted values for the primary variable, each forecasted value being associated with one of a series of future time points; characterized in that the processor (11) is configured to, for at least one of the future time points, predict (S33) a value for the primary variable using data of at least one secondary variable captured by a subset of the set of sensors, compare (S34) the predicted value to the forecasted value associated with the future time point, and switch (S38) to a different subset of the set of sensors, if the predicted value deviates from the forecasted value with more than a specified threshold value.

Item 20: Computer-readable storage medium, comprising instructions which, when executed by a computer, cause the computer to carry out the method of any one of claims 1-18.

While the device and the method for monitoring have been described in connection with what is presently considered to be the most practical embodiments, it is to be understood that the device and the method are not to be limited to the disclosed embodiments, but on the contrary, are intended to cover various modifications and equivalent arrangements included within the spirit and the scope of the appended claims.

What is claimed is:

1. A method for monitoring a primary variable, the method being carried out in a device having access to a set of sensors, comprising
    receiving, from a network service, a series of forecasted values for the primary variable, each forecasted value being associated with one of a series of future time points; and;
    for at least one of the future time points, predicting a value for the primary variable using data of at least one secondary variable captured by a subset of the set of sensors, comparing the predicted value to the forecasted value associated with the future time point, and switching to a different subset of the set of sensors, if the predicted value deviates from the forecasted value with more than a specified threshold value.

2. A method according to claim 1, wherein the predicting and the comparing are repeated for a subsequent future time point using the same subset of the set of sensors, if the predicted value deviates from the forecasted value with less than the specified threshold value.

3. A method according to claim 1, wherein a predetermined number of subsets of the set of sensors are ordered in a predetermined order and wherein switching to a different subset of the set of sensors comprises switching to the next subset according to the predetermined order.

4. A method according to claim 3, wherein the predetermined order is based on prediction confidence.

5. A method according to claim 3, wherein the predetermined order is based on power conservation.

6. A method according to claim 3, wherein the predetermined order is based on power consumption.

7. A method according to claim 3, wherein the predetermined order is received from the network service.

8. A method according to claim 3, wherein at least one sensor in the set of sensors is included in more than one subset in the predetermined order of subsets.

9. A method according to claim 1, comprising reporting to the network service, if a specified number of subsets of the set of sensors has been used.

10. A method according to claim 1, comprising reporting to the network service if the difference between the predicted value and the forecasted value exceeds a predetermined reporting threshold value.

11. A method according to claim 9, comprising receiving, in response to the reporting, an updated series of forecasted values for the primary variable.

12. A method according to claim 9, wherein at least one subset of sensors comprises a sensor for measuring the primary variable, and reporting comprises reporting a current value of the primary variable to the network service.

13. A method according to claim 1, wherein receiving comprises receiving a series of threshold values.

14. A method according to claim 13, wherein each threshold value of the series of threshold values is associated with a future time point.

15. A method according to claim 13, wherein at least two threshold values in the series of threshold values are different.

16. A method according to claim 1, comprising receiving, from the network service, a prediction model, and using the prediction model for predicting the value of the primary variable using data of at least one secondary variable captured by a subset of the set of sensors.

17. A method according to claim 16, wherein the prediction model is based on at least one of a linear regression model, a recurrent neural network, a classification model, a support-vector machine and a random forest algorithm.

18. A method according to claim 1, wherein the primary variable is a blood glucose level.

19. A device for monitoring a primary variable, comprising a processor and a communication interface, the device having access to a set of sensors, wherein the communication interface is configured to receive, from a network service, a series of forecasted values for the primary variable, each forecasted value being associated with one of a series of future time points; wherein the processor is configured to, for at least one of the future time points, predict a value for the primary variable using data of at least one secondary variable captured by a subset of the set of sensors, compare the predicted value to the forecasted value associated with the future time point, and switch to a different subset of the set of sensors, if the predicted value deviates from the forecasted value with more than a specified threshold value.

20. A non-transitory computer-readable storage medium, comprising instructions which, when executed by a computer, cause the computer to carry out the method of claim 1.

* * * * *